United States Patent [19]
Paratte

[11] Patent Number: 4,782,827
[45] Date of Patent: Nov. 8, 1988

[54] ORTHOPEDIC APPARATUS

[76] Inventor: Bernard Paratte, 23 Général-Dufour, 2300 La Chaux-de-Fonds, Switzerland

[21] Appl. No.: 804,859

[22] Filed: Dec. 5, 1985

[51] Int. Cl.$^4$ ................................................ A61F 5/00
[52] U.S. Cl. .................... 128/80 R; 5/444; 128/84 R
[58] Field of Search ............... 5/444, 505; 128/80 R, 128/84 R, 86, 88, 135, 382; 297/439

[56] References Cited

U.S. PATENT DOCUMENTS

| | | | |
|---|---|---|---|
| 1,904,942 | 4/1933 | Heigl | 128/84 R |
| 2,844,143 | 7/1958 | Swanson | 128/84 R |
| 3,086,522 | 4/1963 | Frohmader | 128/80 J |
| 3,345,654 | 10/1967 | Noble | 5/444 |

FOREIGN PATENT DOCUMENTS 128115  12/1984  European Pat. Off. .......... 128/80 R Primary Examiner—Stephen F. Husar
Attorney, Agent, or Firm—Marks Murase & White

[57] ABSTRACT

The apparatus comprises a base in slots of which two posts are removably mounted. One post is provided for supporting an orthopedic support in form of a shoe and the other post for supporting a set of two cradle splints. The cradle splints are pivotably coupled together by means of a hinge joint. A mechanism is provided for permitting adjustment of the mutual distance between the cradle splints as well as of their mutual angle of inclination. One cradle splint supports the calf and the other the thigh of a patient. The set of two cradle splints may be further adjusted at a given distance above the base and the angle of inclination of the cradle splint supporting the calf may be adjusted with respect to the plane of the base. The orthopedic support may be angularly adjusted in the plane of the sole and in a sagittal plane perpendicular thereof. Extension pieces may be provided in the case of extension of the leg. The apparatus has a great number of applications in the field of orthopedy.

20 Claims, 8 Drawing Sheets

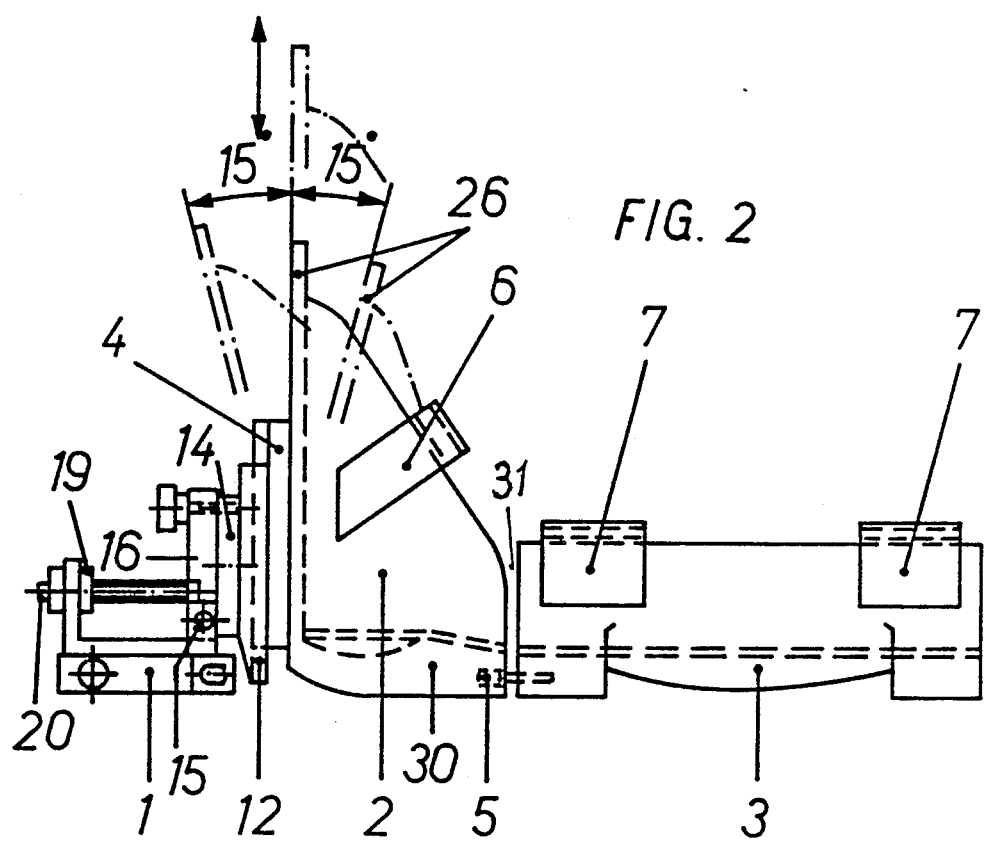
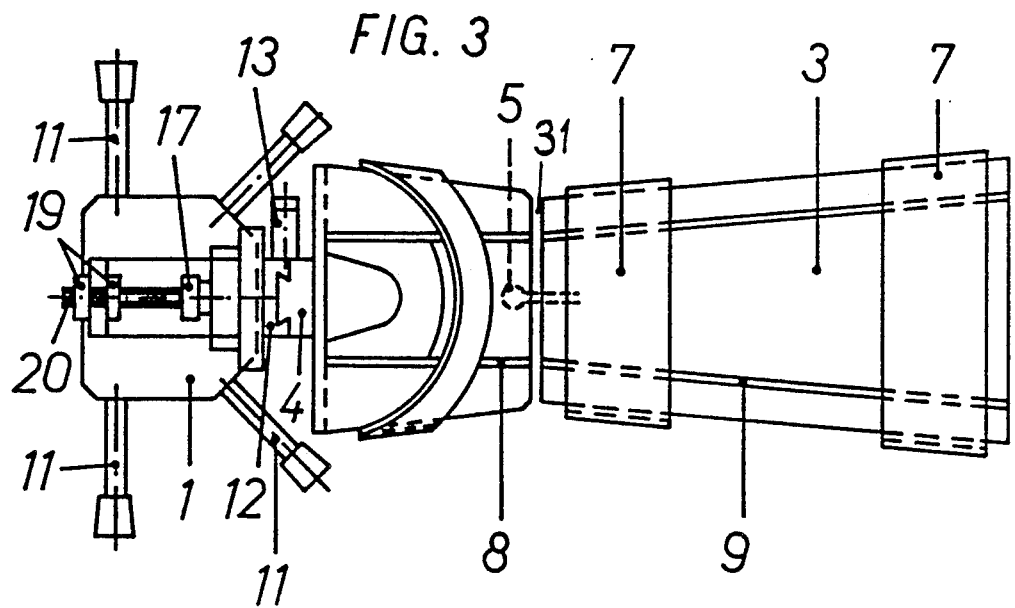

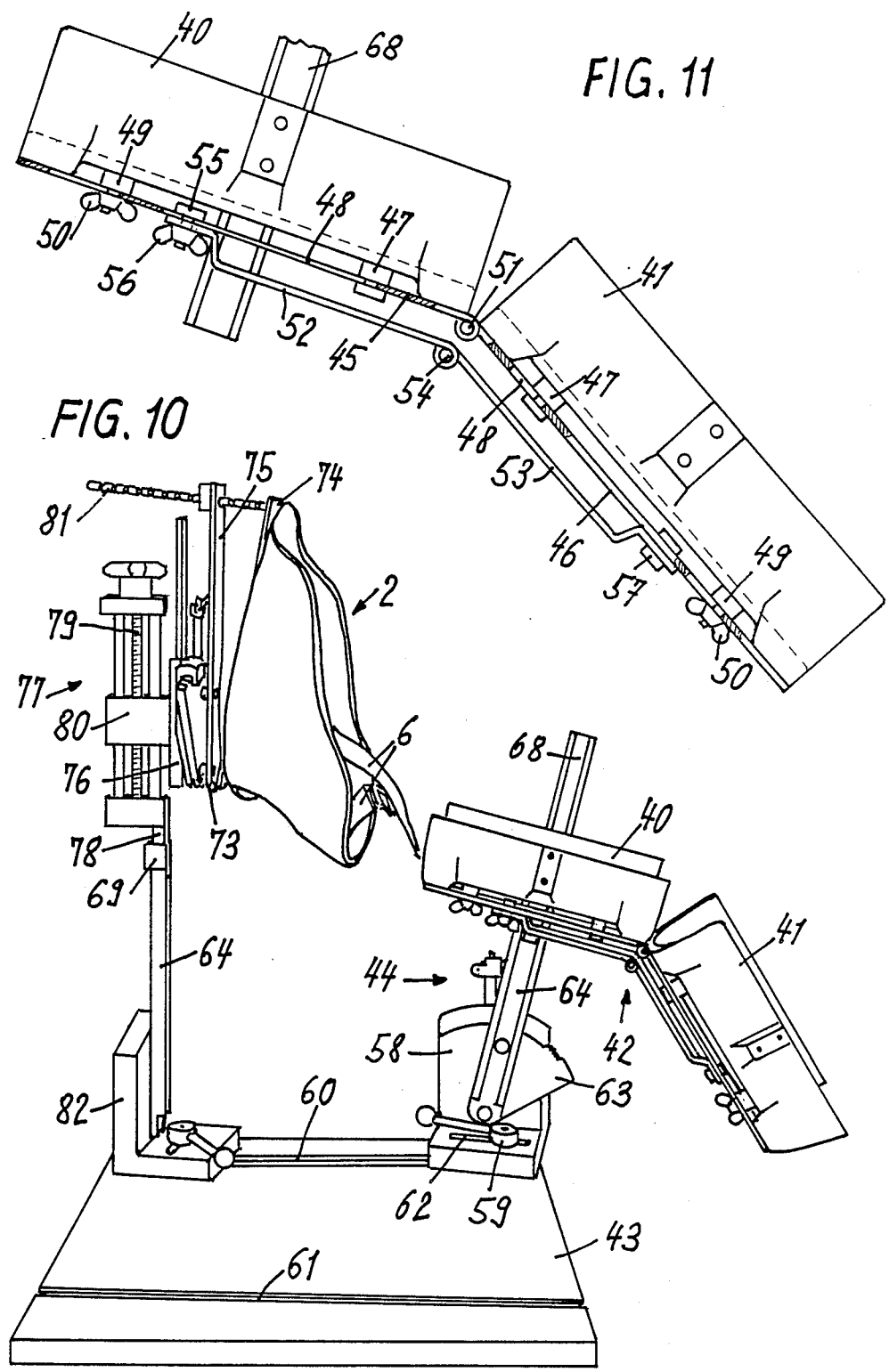

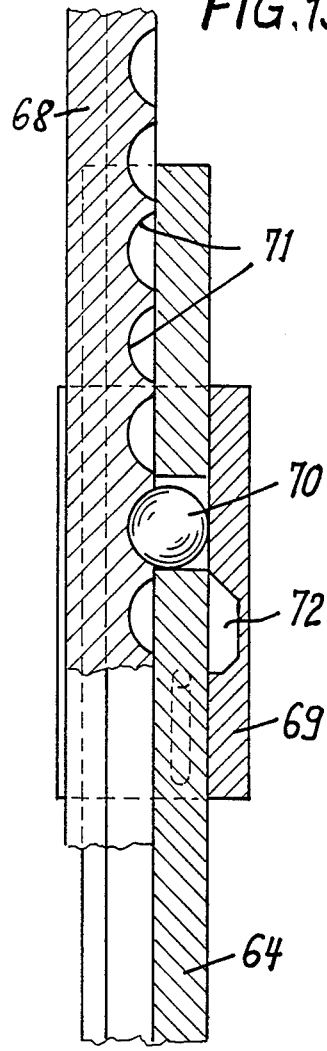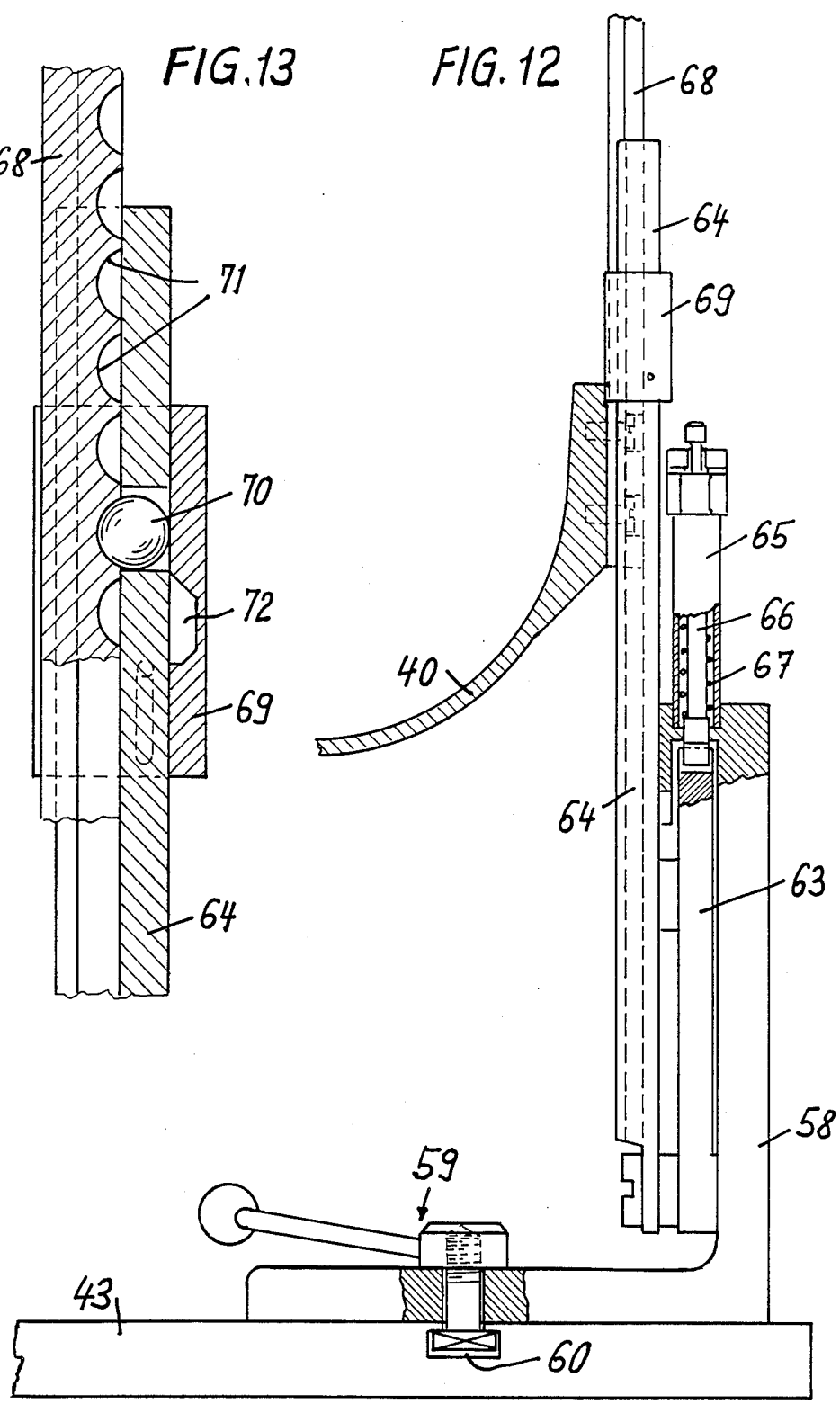

ORTHOPEDIC APPARATUS

BACKGROUND OF THE INVENTION

The present invention relates to an orthopedic apparatus comprising at least one orthopedic support having a resting surface of at least approximately spherical shape for resting on a patient's bed, said orthopedic support comprising a sole extending beyond the toes of the patient for receiving the plantar surface of the foot and for supporting the weight of the bedclothes and coverlets and at least one clamp for removably fastening said orthopedic support to the foot.

Such an apparatus is known from the U.S. Pat. No. 3,345,654. It does not comprise means for orienting the foot of the patient with respect to the leg nor any means for supporting the calf. U.S. Pat. No. 3,892,231 discloses a foot and leg correctional device for correcting the inclination or deformity of the bones, particularly for infants. The device is in form of a shoe in two parts, the front part being capable of being oriented with respect to the rear part in a sagittal plane and in a plane perpendicular thereof. The device does not include any means for supporting the calf and it is not intended for maintaining the foot or the leg of a patient lying in a bed, in a given position in order to relieve this patient.

SUMMARY OF THE INVENTION

It is therefore an object of the present invention to realize an orthopedic apparatus permitting to support the foot and the calf and/or the thigh and to maintain the foot or the leg of a lying patient in a given, adjustable position as desired by the physician for relieving the patient before or after a surgical procedure of the foot, the leg, and knee or the hip. The apparatus must be such that the heel is not in contact with the bed.

To solve this problem, the apparatus according to the invention further comprises a cradle splint loosely coupled to the orthopedic support for supporting the calf and for positioning the calf with respect to the orthopedic support and a base member capable of being removably coupled to the orthopedic support, the base member comprising an adjusting means for orienting the orthopedic support in the plane of the sole and in a sagittal plane. The cradle splint for supporting the calf is loosely coupled to the orthopedic support so that it may be adapted to the orthopedic support in any orientation within a determined solid angle. The base comprises adjusting means for permitting adjustment of the inclination of the orthopedic support in the plane of the sole and in a sagittal plane perpendicular thereof, such that the position of the foot relative to the leg can be adjusted in accordance with the physician's instructions. The orthopedic support may be adjusted vertically such that it can be adapted to the level of the base independently of the inclination of the sole with respect to the base. The sole which projects beyond the toes supports the weight and pressure of the bedclothes and coverlets on the toes of the patient.

A second embodiment of the apparatus of the invention comprises at least one orthopedic support with a sole extending beyond the toes of a patient for receiving the plantar surface of the foot and for supporting the bedclothes and coverlets and with at least one clamp for removably fastening the orthopedic support to the foot. A means for removably mounting the orthopedic support on a base and for adjusting the distance between said orthopedic support and the base. Additionally, the apparatus includes a means for orienting orthopedic support in the plane of the sole and a means for orienting said orthopedic support in a sagittal plane perpendicular to the plane of the sole. A set of two cradle splints are pivotably coupled together for supporting the calf and the thigh respectively. Means are also provided for adjusting the mutual distance of said cradle splints and for adjusting the mutual angle of inclination of said cradle splints.

The set of cradle splints are removably mounted on the base. The distance between the set and the base is adjustable. The angle of inclination of the set with respect to the plane of the base is also adjustable. This second embodiment offers the advantages of supporting the calf as well as the thigh of the patient. The thigh may be supported with a relatively great angle with respect to the plane of the base while the rest of the leg is supported in a horizontal plane. It is also possible to support the entire leg in the stretched position, whereby the foot is supported by the orthopedic support, the calf by the first cradle splint and the thigh by the second cradle splint. This permits extension of the entire leg or of the part of the leg comprised above the knee.

DESCRIPTION OF THE DRAWINGS

FIG. 2 is a lateral view of a first embodiment of the apparatus according to the invention, FIG. 3 is a top view of the apparatus of FIG. 2, FIG. 10 is a lateral view of a second embodiment of the apparatus according to the invention, FIG. 11 is a lateral view of the two cradle splints of the apparatus of FIG. 10, FIG. 12 is a side view partially in section of the support of the cradle splints of the apparatus of FIG. 10, FIG. 13 is a section of a coupling member.

DETAILED DESCRIPTION OF THE INVENTION

Figure 1:
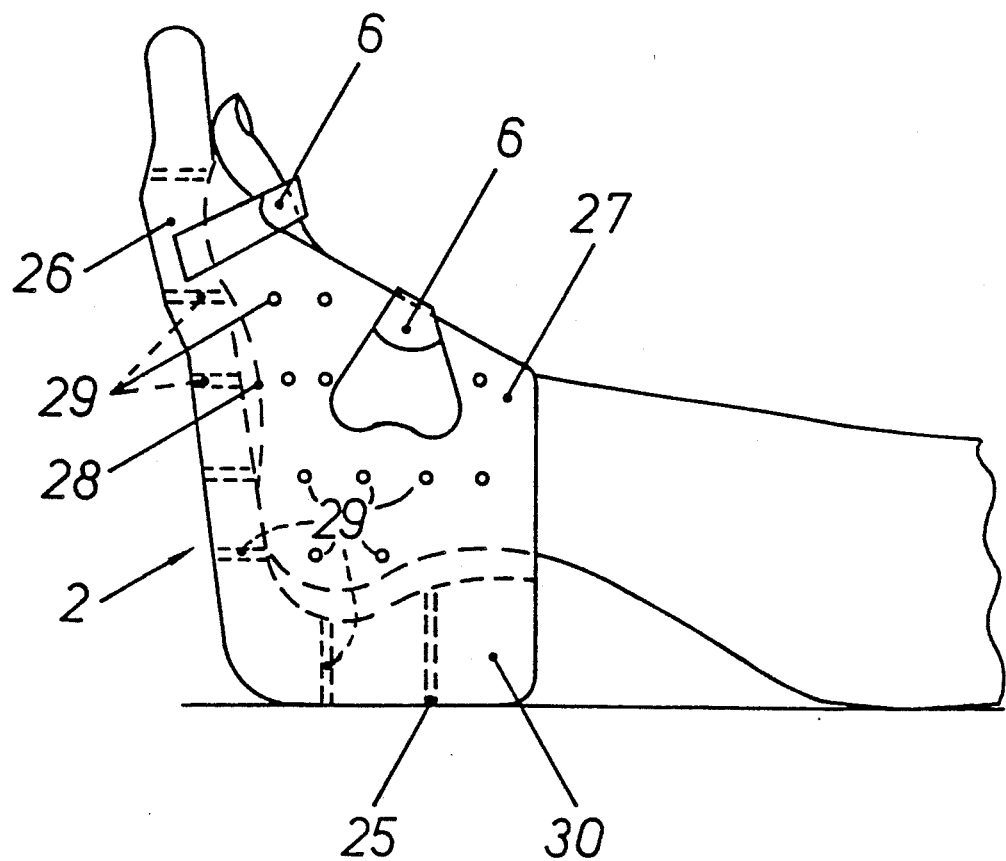
FIG. 1 is a lateral view of an orthopedic support.
Figure 4:
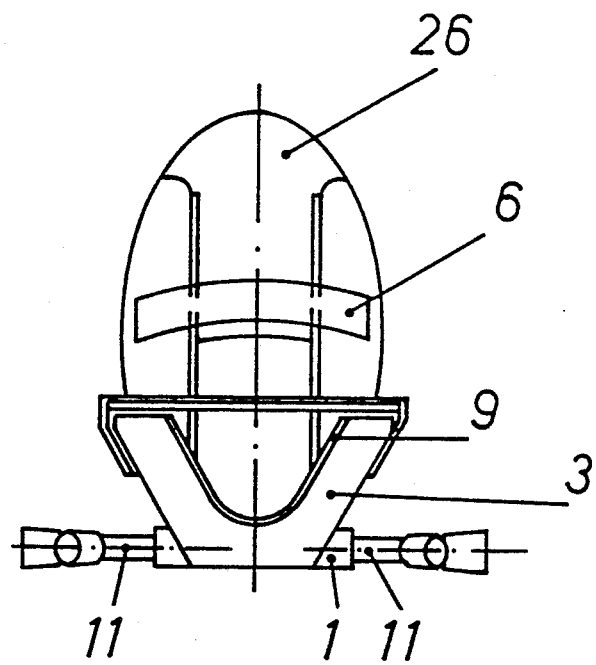
FIG. 4 is a rear view of the apparatus of FIG. 2.

FIG. 1 shows an orthopedic support 2 according to the invention. This support which is of wood or plastic may be utilised alone or in combination with the cradle splint 3 in the case of phlebitis or pain in the leg. In this case, it is preferably utilized by the pair, one support for each foot. It is in form of a front open shoe with lateral walls 27, a sole 26 projecting upwards beyond the toes and a base 30 with an approximately spherical resting surface 25. Ventilation holes 29 may be provided if desired. The sole 26 comprises an orthopedic foot rest 28. The base 30 and the lateral walls 27 are covered at the inside with a removable self adhesive lining 8 (see FIG. 3), e.g. sheepskin, gel cushion, etc. This lining 8 may be easily removed by exerting a pull on it, cleaned and set again in place by means of a simple pressure thus permitting a full hygiene. Self adhesive clamps 6 are provided for fastening the orthopedic support to the foot of the patient. This facilitates and speeds up the setting in place and the removal of the support. The self adhesive lining in the base 30 does not extend up to the sole 26 but it leaves a free space for the heel such that the heel is entirely free, without any contact with the orthopedic support.

FIGS. 2 and 3 show respectively a side view and a top view of the apparatus according to the invention. The apparatus comprises a base member 1 mounted by a slide 12 in a corresponding slideway 4 secured to the sole 26 of the orthopedic support 2 described above. A screw 13 permits to block the slide in the desired position. A cradle splint 3 provided for supporting the calf is removably secured to the base 30 of the orthopedic support 2 by means of a half swivel 5. The cradle splint is of cylindrical or conical shape for receiving the leg. The internal wall of the cradle splint is also covered with a self adhesive lining 9 similar to the lining 8. Self adhesive fastening clamps 7 permit the cradle splint to be removably secured to the leg of the patient. FIGS. 2 and 3 show that a gap 31 is provided between the cradle splint 3 and the orthopedic support 2. This gap as well as the coupling by means of the half swivel 5 permit the cradle splint to be adapted to any orientation with respect to the orthopedic support 2 within a determined solid angle while still being in a horizontal plane. Further, the cradle splint may rotate about its longitudinal axis.

Figure 9:
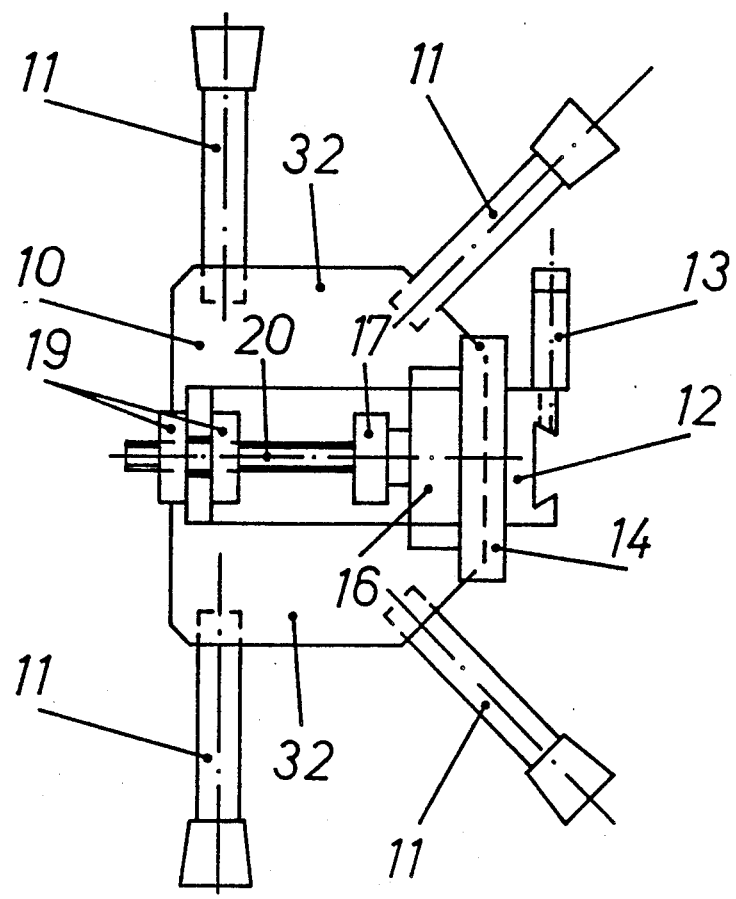

The base member 1 is shown in FIGS. 6 to 9. It comprises a base plate 32 of wood or plastics to which four arms 11 are secured as shown in FIG. 9. These arms provide for good stability of apparatus intended to be utilized in a patient's bed. An angle iron 18 is secured on the base plate 32.

A vertical branch of the angle iron 18 supports in a center slot thereof, a screw 20 by means of a nut and a lock nut 19, the other end of the screw 20 being inserted in a plate 16 and secured in this plate by a pin 33. The screw 20 may rotate about the pin 33. The plate 16 is pivoted about an axis 15 secured between two posts 34 rigidly secured on the horizontal branch of the angle iron 18. A circular plate 14 is rigidly secured to the slide 12 and may rotate with the slide 12 about its axis mounted in the plate 16. The circular plate 14 comprises at its upper end three blind holes 35 schematically shown in FIG. 8 in which the pin shaped end of a stud 17 is engaged. The stud 17 is always pulled toward the slide by a spring (not shown) arranged in the plate 16.

Figure 5:
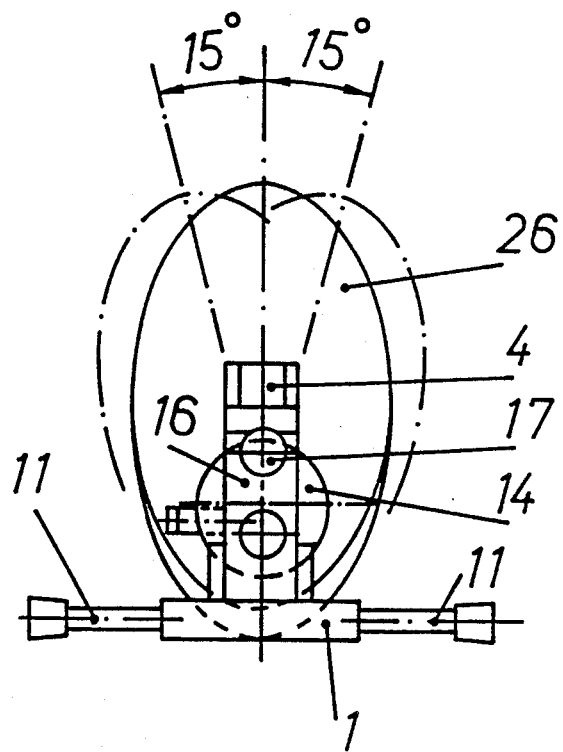
FIG. 5 is a front view of the apparatus of FIG. 2, FIGS. 6 to 9 show the base of the apparatus respectively from the rear, the side, the front and the top.
Figure 6:
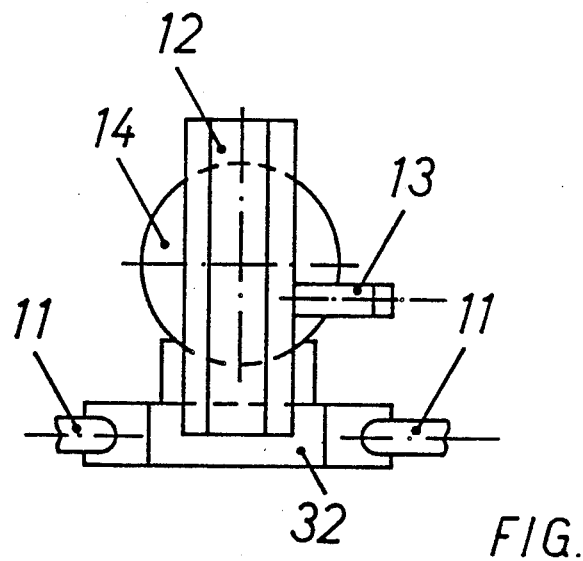
Figure 8:
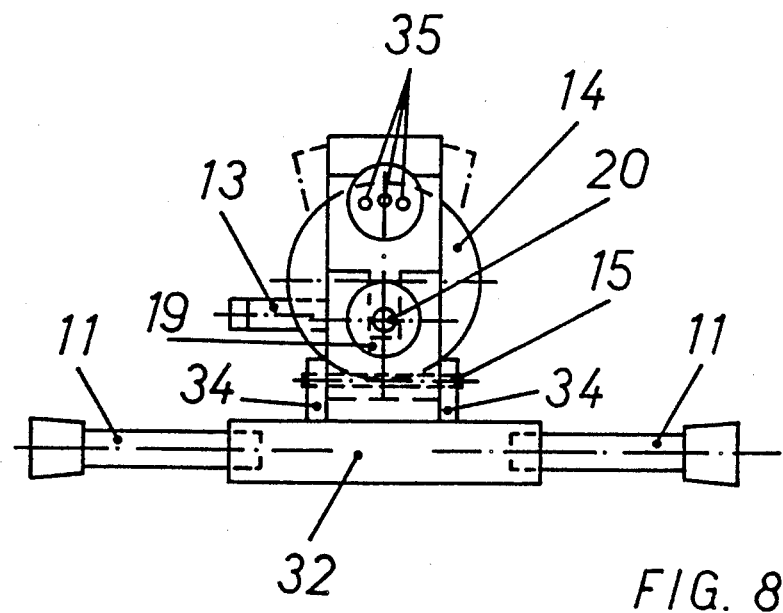
Figure 7:
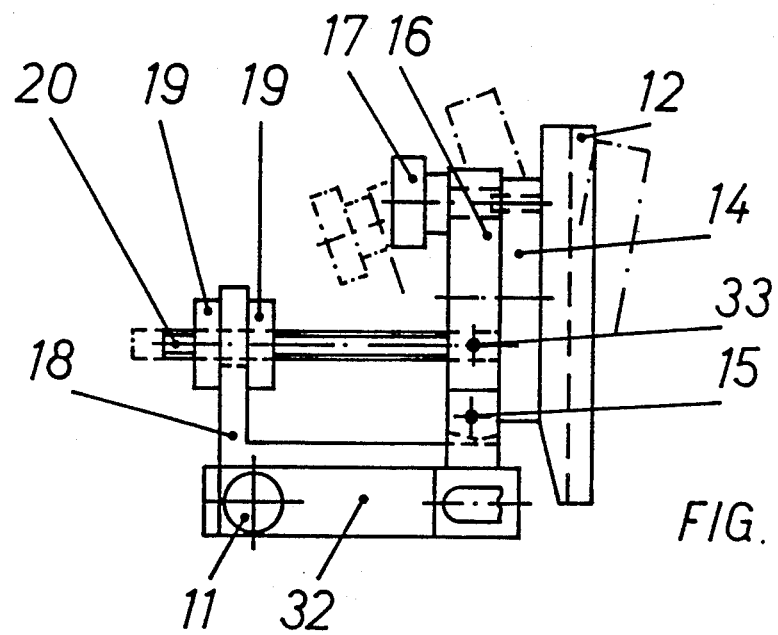

The device described above permits different spatial orientation of the slide 12 and consequently of the orthopedic support 2 secured on this slide. When the stud 17 is engaged in the central hole 35 of the circular plate 14, the sole 26 of the orthopedic support is in the center position shown in full line in FIG. 5. If the stud 17 is retracted against the recalling force of the spring, the circular plate 14 is liberated and it is possible to rotate it about its axis, e.g. but not in excess of 15° toward the left or the right with respect to the central position and to lock it in each of these end positions by releasing the stud 17 the end of which then engages the corresponding blind hole 35 which locks the circular plate 14 and the slide in this extreme position. Consequently, the sole 26 is in one or the other of the extreme positions shown in dash-dotted lines in FIG. 5, these extreme positions being respectively angularly shifted 15° with respect to the center position in the example described. The preceeding shows that the orthopedic support may be angularly adjusted in three positions in the plane of the sole 26.

By releasing the nut and lock nut 19, the left end of the screw 20 (FIG. 2 or 7) is liberated which permits tipping the plate 16 forward or backward about the axis 15 with the circular plate 14, the slide 12 and the orthopedic support 2. With respect to the median position as shown in FIG. 2 with the sole 26 lying in a vertical plane, it is possible to tip the orthopedic support forward or backward in the sagittal plane, e.g. 15° forward or backward. In each case, the slide 12 permits adjustment of the height of the orthopedic support such that its base 30 is at the level of the base plate 32.

It is to be seen that adjustment of the orthopedic support in the sagittal plane by means of the screw 20, the nut and lock nut 19 is continuous. The adjustment in the plane of the sole is discontinuous because only three indexing positions are foreseen. It is clear however that this adjustment in the plane of the sole can be made continuous e.g. by means of an endless screw and that the adjustment in the sagittal plane can be easily made discontinuous. As well, the slide 12, 4 can be replaced by a system with a cylinder and a piston without departing from the general idea of the invention. The angular displacements in the plane of the sole and in the sagittal plane are not limited to + or −15° but they can have any other desired value.

The FIGS. 10 to 14 show a second embodiment of the apparatus according to the invention. FIG. 10 shows that the apparatus comprises an orthopedic support 2 which is identical to the one of FIG. 1 and two cradle splints 40 and 41 coupled together by a mechanism 42 permitting to adjust the distance between them and their relative angular position. The two cradle splints are not coupled to the orthopedic support 2 and they are mounted on a common base 43 of rectangular shape by means of a support 44. FIG. 11 shows how the cradle splints 40 and 41 are coupled together. Each cradle splint is mounted on a list 45 and 46, respectively by means of a tenon 47 which engages a median slot 48 of the list by means of a bolt 49 with a wing nut 50 which, when tightened, hinders any displacement of the cradle splint with respect to the list. The lists 45, 46 are joined together by a hinge joint 51. When loosening the wing nuts 50, the cradle splints may be shifted longitudinally along their respective lists 45, 46. The cradle splint 41 is normally provided for supporting the thigh and the cradle splint 40 for supporting the calf. The longitudinal displacement of the cradle splints permit precise adjustment their position on the thigh and the calf and adaption of their mutual distance to the leg of the patient. The lists 45, 46 are further connected together by strips 52 and 53 coupled together by a hinge joint 54, these strips being at a certain distance from the lists 45, 46. The other extremity of the strip 52 is bent to contact the corresponding list 45 and is removably secured to this list by means of a bolt 55 which engages the median slot 48 using a wing nut 56. The other extremity of the strip 53 is bent to contact the list 46 and it is firmly secured to this list by a rivet 57. This permits by loosening the wing nut 56 to change the relative angular position of the cradle splints 40, 41. During this operation the list 45 moves toward the left or the right in FIG. 11 with respect to the bolt 55. When the desired angular position is obtained the wing nut 56 is tightened and the adjustment is completed.

FIG. 10 shows further that the support 44 is mounted on the base 43 by means of angle iron 58 with a blocking mechanism 59. The angle iron 58 is displaceable along a slot 60 of the base 43 which comprises a second slot 61 provided for a second orthopedic apparatus. The angle iron 58 may be displaced laterally in a slot 62 and pivoted about the axis of the blocking mechanism 59. A post 64 with two grooves is secured to a toothed sector 63 (see also FIG. 12) and pivotably mounted at the base of the vertical branch of the angle iron 58. FIG. 12 shows that a tube 65 is secured to the top part of the vertical branch of the angle iron 58. The tube 65 comprises a rod 66 normally urged downwards by a spring 67. The end part of the rod engages between two neighbouring teeth of the sector 63 for blocking the sector in a determined angular position. For changing this angular position, the rod 66 is retracted upwards against the force of the spring by a mechanism not shown. The cradle splint 40 comprises a T-shaped rail 68 engaging in the grooves of the post 64. As shown in FIG. 13, the height of the cradle splint with the rail 68 may be adjusted with respect to the base 43. To this end, a housing 69 comprising a retractible ball 70 is provided on the post 64. In the position indicated in FIG. 13, the ball 70 engages in one of several blind holes of spherical shape 71 thus locking the rail 68 and the post 64 together. When the housing 69 is urged upwards, the ball 70 enters a recess 72 of the housing and the rail 68 may be displaced along the post 64. This permits adjustment of the distance of the set of cradle splints 40 and 41 with respect to the base 43. By means of the toothed sector 63 and the mechanism 65-67, the angle of inclination of the set of cradle splints may be adjusted with respect to the plane of the base 43.

FIG. 10 shows also that the orthopedic support 2 is secured on a list 74 which is pivotably mounted at its lower extremity to a hinge joint 73. The stationary part of the hinge joint is secured to a post 75 attached itself to a toothed sector sector 63 pivotably mounted at the base of a support member 76. In FIG. 10, the support 76 is secured to an extension piece 77 which is inserted in a post 64. The distance of the extension piece 77 above the base 43 may be adjusted as previously described by a housing 69 comprising a retractible ball engaging one of several blind holes of spherical shape provided in a rail 78 at the lower part of the extension piece 77. By means of a screw 79 and a sliding piece 80 secured to the support member 76, the distance of the orthopedic support above the base 43 may be precisely adjusted. However, the extension piece is optional. If the support member 76 comprises a rail similar to the rail 68 of the cradle splint 40, the orthopedic support may be directly mounted in the post 64. A rod 81 secured to the upper part of the list 74 and engaged in an opening at the upper part of the post 75 permits the orthopedic support to be oriented in the sagittal plane. The post 64 supporting the orthopedic support is rigidly mounted to angle iron 82 with a blocking mechanism similar to the one of the angle iron 58. It is also possible to mount a second extension 77 in the post 64 supporting the set of cradle splints 40 and 41.

The preceding shows that the second embodiment of the apparatus comprises several possibilities of adjustments of the different positions of the apparatus. The orthopedic support is adjustable vertically above the base 43, in the plane of the sole and in the sagittal plane independently from the set of cradle splints. The mutual angle of inclination of the cradle splints and their mutual distance are adjustable and both cradle splints, when adjusted in the same plane can be brought in a horizontal plane or in an plane inclined with respect to the base 43. The axis of the cradle splints may also be adjusted in a desired direction with respect to the axis of the orthopedic support by means of the angle iron 58. Both extension pieces 77 are utilized when it is desired that the thigh supported by the cradle splint 41 has a strong angle of inclination with respect to the base 43 while the rest of the leg is to be set in a horizontal plane or when the whole leg must be strongly inclined with respect to the plane of the base 43.

Figure 14:
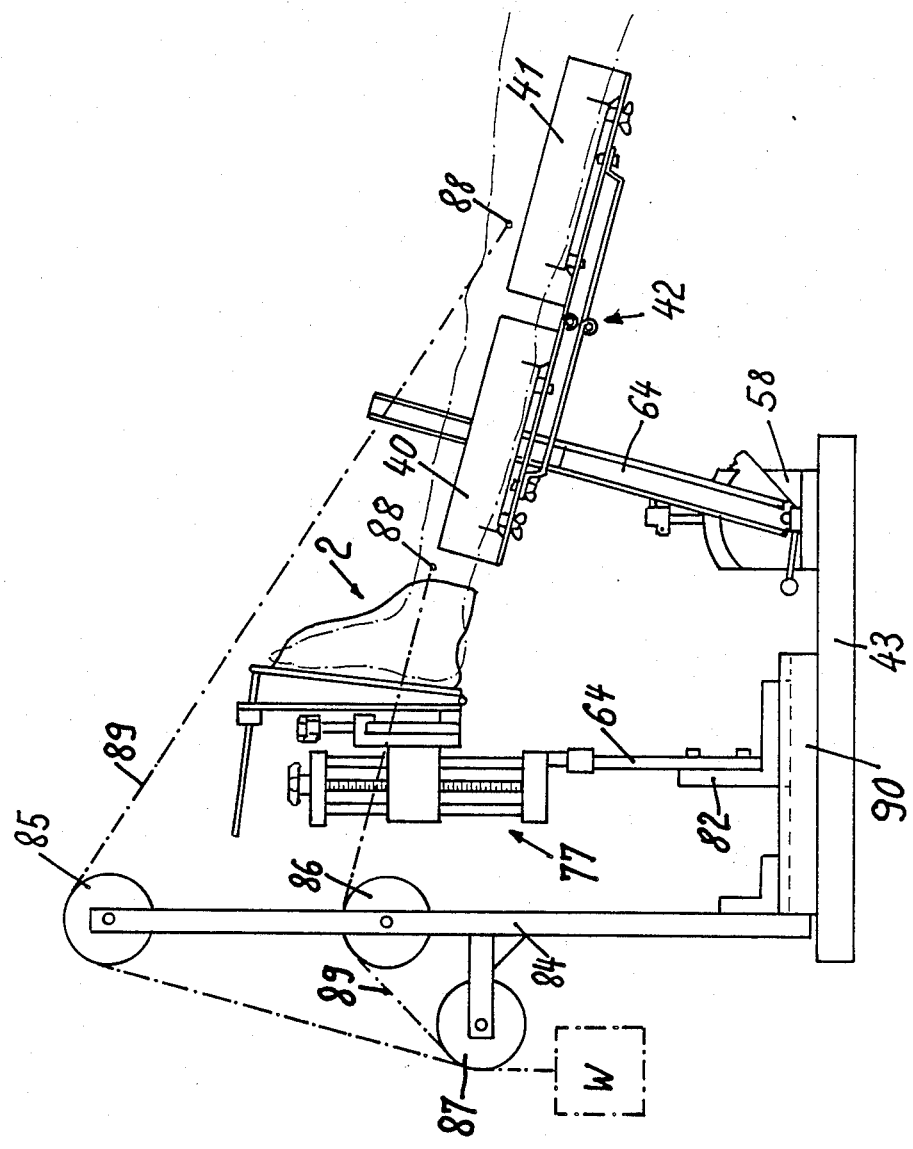
FIG. 14 shows an utilization of the apparatus of FIG. 10 for an extension of the leg or of the part of the leg above the knee.

The apparatus as described above is well suited to be used in the case of extension of the entire leg of a patient or of extension of the part of the leg above the knee. FIG. 14 shows the utilization of the apparatus of FIG. 10 in case of extension. A vertical support 83 with a crosspiece 84 is secured at one side of the base 43. The support 83 comprises an upper pulley 85, an intermediate pulley 86 and a pulley 87 at the free end of the crosspiece 84. The angle iron 82 supporting the orthopedic support 2 is slidably mounted in a slideway 90 secured on the base 43. In the case of the extension of the entire leg, a nail 88 is inserted in the leg near the ankle and a rope 89 attached to the nail is passed on the intermediate pulley 86 and the pulley 87. A weight W is attached to the end of the rope for providing the required extension force. Normally, the weight W is of 1/10 of the weight of the patient. FIG. 14 shows that in the case of extension the leg is in a stretched position so that the orthopedic support and both cradle splints are arranged in the same direction. In the case of extension of the part of the leg above the knee, the nail 88 is provided in the leg above the knee and the rope 89 is passed over the top pulley 85. The crosspiece 84 is provided for ensuring that the weight W is outside of the bed of the patient.

The apparatus according to the present invention can be utilized for supporting the foot and the leg before or after a surgical procedure of the foot, the leg, the knee, the thigh or the hip and in the case of flabby paralysis or cerebral apoplexy for maintaining the feet of an unconscious patient in a correct position, in order to prevent an ulterior permanent deformation of the leg which would prevent the heel from resting on the ground.

The apparatus according to the invention may be manually adjusted without any tool or accessories. By utilizing the embodiment of FIGS. 10 to 13, the apparatus avoids formation of eschars to the heels, supresses the problem of equin, relieves pain in cases of phlebitis or thrombosis, and places the leg in postoperative position in case of ligaments laceration. The apparatus may further be utilized in case of fractures of the leg or in the case of a leg operation. The additional extension pieces 77 are more particularly intended for being utilized in paraplegic institutions or for special purposes. Due to the fact that the mechanism 42 may be of non-metallic components, it is possible to make radiographs of the leg while being supported by the apparatus.

I claim:
1. An orthopedic apparatus comprising:
 an orthopedic support means for supporting a foot, said orthopedic support means comprising a sole means extending in a first plane beyond the toes for receiving a plantar surface of the foot and for supporting any overlying bedclothes and coverlets;
 a clamp means for removably fastening said orthopedic support means to the foot;
 first means for removably mounting said orthopedic support means on a base extending in a second plane and for adjusting a distance between said orthopedic support means and the base;
 second means for orienting said orthopedic support means in said first plane;

third means for orienting said orthopedic support means in a sagittal plane perpendicular to said first plane;

a set of first and second cradle splint means pivotably coupled for supporting respectively a calf and a thigh;

fourth means for adjusting a distance between said cradle splint means;

fifth means for adjusting an angle of inclination of said cradle splint means;

sixth means for removably mounting said set of cradle splint means on said base and for adjusting a distance between said set of cradle splint means and said base; and seventh means for adjusting an angle of inclination of said set of cradle splint means with respect to said second plane.

2. An apparatus according to claim 1, wherein said first and second cradle splint means are mounted on first and second list means, respectively, each list means comprising a median slot, said list means being pivotably coupled together; and wherein each cradle splint means comprises a guiding means engaging in said median slot and a fastening means provided on said guiding means for removably fastening each of said cradle splint means to their respective list means, said cradle splint means being displaceable along said list means for adjustment of a distance therebetween.

3. An apparatus according to claim 2, further comprising:

first and second strip means associated with said first and second list means, said strip means being pivotably coupled at respective first ends at a first distance from said list means;

guiding means engaged in said median slot, said first strip means being fastened at a second end to said first list means by said guiding means;

fastening means provided on said guiding means for removably fastening said first strip means to said first list means, said second strip means being firmly fastened at a second end to said second list means;

wherein adjustment of a relative displacement of said first strip means with respect to said first list means permits adjustment of a mutual angle of inclination of said cradle splint means.

4. An apparatus according to claim 1, wherein said sixth means comprises:

a supporting means adapted to be removably mounted in the base;

a post means with two lateral grooves, said post means being secured to said supporting means;

a rail means connected to one of said cradle splint means and engaging in said lateral grooves, said rail means having a plurality of first recesses;

a housing means, slidably mounted on said post means and comprising an internal recess and a ball member, for selectively displacing said ball member into said first recesses and into said internal recess;

wherein said housing removably locks said rail to said post means when said ball member engages one of said first recesses; and said rail means being displaceable in said grooves along said post means when said ball member engages said internal recess.

5. An apparatus according to claim 4, wherein said seventh means comprises:

a toothed sector secured to said post means, said post means being pivotably mounted with said toothed sector to said supporting means;

stop means, provided on said supporting means and adapted to be removably engaged between successive teeth of said toothed sector for maintaining said toothed sector and said rail means in a determined angular position with respect to said second plane.

6. An apparatus according to claim 4, further comprising:

at least one extension means for supporting said orthopedic support, said extension means comprising a guide means at its lower part for insertion in said lateral grooves of said post means, said guide means being secured to said post means by said housing means, for removably securing said extension means to said post means.

7. An apparatus according to claim 4, comprising a second extension means for supporting said set of cradle splint means.

8. An apparatus according to claim 1, wherein said base comprises a second slot for receiving a second orthopedic apparatus.

9. An apparatus according to claim 1, further comprising:

first and second supporting means for supporting said orthopedic support and said set of cradle splint means, respectively, said first and second supporting means being adapted to be shifted along a slot of said base, and adapted to be shifted laterally with respect to said slot, and adapted to rotate about an axis perpendicular to the plane of said base, said first and second supporting means comprising blocking means for firmly attaching said supporting means to said base.

10. An orthopedic apparatus comprising:

orthopedic support means for supporting a foot having a plantar suface, said orthopedic support means having a sole means for receiving on an upper surface thereof the plantar suface of the foot;

a cradle splint operatively coupled to said orthopedic support means;

first positioning means coupled to said orthopedic support means for adjusting the position of said orthopedic support means in a plane substantially perpendicular to said sole;

second positioning means coupled to said orthopedic support means for adjusting the position of said orthopedic support means in a plane substantially parallel to said sole; and means coupled to said cradle splint for adjusting the position of said cradle splint with respect to said orthopedic support means;

a pedestal means;

a first mounting means for removably mounting said orthopedic support to said pedestal;

a second mounting means for removably mounting said cradle splint to said pedestal; and an adjusting means disposed on said pedestal for adjusting a distance between said cradle splint and said orthopedic support.

11. An apparatus according to claim 10, wherein:

said first positioning means comprises a first pivoting means for pivoting said sole about a first axis extending substantially parallel to the plane of said sole; and said second positioning means comprises a second pivoting means for pivoting said sole about a second axis substantially perpendicular to said sole.

12. An apparatus according to claim 11, wherein:
said first pivoting means comprises a rod coupled to said sole and extending substantially perpendicular to said first axis; and
said second pivoting means comprises a plurality of notches and a latching means for latching with one of said notches.

13. An apparatus according to claim 10, wherein said cradle splint comprises:
a calf splint means for supporting the calf portion of a leg;
a thigh splint means for supporting a thigh portion of the leg;
a hinge means for pivotably coupling said calf splint means and said thigh splint means; and
first and second list means for slideably receiving said calf and thigh splint means, respectively.

14. An apparatus according to claim 13, wherein said second mounting means comprises:
a longitudinal post means for elevating said cradle splint at a variable height above said pedestal; and
a pivoting means for pivoting said longitudinal post about an axis extending along a plane of said pedestal.

15. An apparatus according to claim 10, further comprising a longitudinal post means for elevating said orthopedic support at a variable height above said pedestal;
wherein said second positioning means comprises a list means mounted on a lower surface of said sole and pivotably mounted to said longitudinal post, and an engaging means for selectively engaging said list means in a fixed position;
wherein said first positioning means comprises a rod extending from said list means whereby pulling on said rod induces clockwise rotation on said sole and pushing on said rod induces counter-clockwise rotation of said sole.

16. An apparatus according to claim 14, further comprising:
a vertical support slideably mounted on said pedestal;
a cross-piece extending substantially horizontally from said vertical support;
a first pulley mounted at an upper portion of said vertical support; and
a second pulley mounted at a middle portion of said vertical support;
wherein said first mounting means comprises a longitudinal post means for elevating said orthopedic support at a variable height above said pedestal;
wherein said first positioning means comprises a list means mounted on a lower surface of said sole and pivotably mounted to said longitudinal post and an engaging means for selectively engaging said list in a fixed position; and
wherein said second positioning means comprises a rod extending from said list means, whereby pulling on said rod induces clockwise rotation of said sole and pushing on said rod induces counter-clockwise rotation of said sole.

17. An apparatus according to claim 16, further comprising:
a third pulley mounted at a free end of said cross-piece;
a first flexible cable having a weight attached to a first free end thereof, said first cable extending around said third pulley and said first pulley and adapted to be attached at a second free end thereof to a leg resting in said apparatus; and
a second flexible cable attached at a first free end thereof to said weight and extending around said third pulley and second pulley and adapted to be attached at a second free end thereof to a leg resting in said apparatus.

18. A method of supporting a lower portion of a limb comprising the steps of:
(a) providing an orthopedic support means for supporting a foot, said orthopedic support means comprising a sole means extending in a first plane beyond the toes for receiving a plantar surface of the foot and for supporting any overlying bedclothes and coverlets;
(b) removably fastening said orthopedic support means to the foot;
(c) removably mounting said orthopedic support means on a base extending in a second plane;
(d) adjusting a distance between said orthopedic support means and the base;
(e) orienting said orthopedic support means in said first plane;
(f) orienting said orthopedic support means in a sagittal plane perpendicular to said first plane;
(g) providing a set of first and second cradle splint means pivotably coupled for supporting respectively a calf and a thigh;
(h) adjusting a distance between said set of cradle splint means;
(i) adjusting an angle of inclination of said set of cradle splint means;
(j) removably mounting said set of cradle splint means on said base;
(k) adjusting a distance between said set of cradle splint means and said base; and
(l) adjusting an angle of inclination of said set of cradle splint means with respect to said second plane.

19. The method according to claim 18, further comprising the steps of:
(a) providing a vertical support means slidably mounted on said base;
(b) providing first and second pulley means mounted at upper and middle portions of said vertical support means;
(c) attaching a mass via a flexible connecting means to a limb supported by said set of cradle splints;
(d) aligning said flexible connecting means along said first and second pulley means.

20. An orthopedic apparatus comprising:
(a) an orthopedic device, said orthopedic device comprising:
orthopedic support means for supporting a foot having a plantar suface, said orthopedic support means having a sole means for receiving on an upper surface thereof the plantar surface of the foot;
a cradle splint operatively coupled to said orthopedic support means;
first positioning means coupled to said orthopedic support means for adjusting the position of said orthopedic support means in a plane substantially perpendicular to said sole;
second positioning means coupled to said orthopedic support means for adjusting the position of said orthopedic support means in a plane substantially parallel to said sole; and
means coupled to said cradle splint for adjusting the position of said cradle splint with respect to said orthopedic support means; and (b) a mounting means for removably mounting said orthopedic device to a pedestal;
wherein a distance between said orthopedic device and the pedestal is variable.

* * * * *